ered clay or crystalline aluminosilicate catalysts. The method involves promoting the activity by adding a strong acid.

United States Patent [19]
Gregory et al.

[11] 4,440,958
[45] Apr. 3, 1984

[54] METHOD FOR PROMOTING THE ACTIVITY OF CATION-EXCHANGEABLE LAYERED CLAY AND ZEOLITE CATALYSTS IN PROTON-CATALYSED REACTIONS

[75] Inventors: Reginald Gregory, Camberley; David J. Westlake, Woking, both of England

[73] Assignee: The British Petroleum Company Limited, London, England

[21] Appl. No.: 288,019

[22] Filed: Jul. 29, 1981

[30] Foreign Application Priority Data

Aug. 1, 1980 [GB] United Kingdom ............... 8025259

[51] Int. Cl.³ ............................................. C01C 67/04
[52] U.S. Cl. .................................. 560/247; 560/103; 560/204; 502/85
[58] Field of Search ................. 252/450; 560/247, 96, 560/103

[56] References Cited

U.S. PATENT DOCUMENTS

| | | | |
|---|---|---|---|
| 3,096,365 | 7/1963 | Heisler et al. | 560/247 |
| 3,377,401 | 4/1968 | Newman et al. | 560/247 X |
| 3,492,341 | 1/1970 | Trevillyan | 560/247 |
| 3,535,272 | 10/1970 | Kittrell et al. | 252/450 X |
| 3,617,215 | 11/1971 | Sugahara et al. | 252/450 X |
| 3,836,561 | 9/1974 | Young | 252/450 |
| 3,922,294 | 11/1975 | Leupold et al. | 560/103 X |
| 3,956,183 | 5/1976 | Zuech | 252/450 X |
| 3,997,474 | 12/1976 | Miale et al. | 252/450 |
| 4,059,543 | 11/1977 | Kiovsky et al. | 252/450 X |

FOREIGN PATENT DOCUMENTS 31687  7/1981  European Pat. Off. ............ 560/247

*Primary Examiner*—Carl F. Dees
*Attorney, Agent, or Firm*—Brooks, Haidt, Haffner & Delahunty

[57] ABSTRACT

The activity of cation-exchangeable layered clay or crystalline aluminosilicate catalyst in esterification, etherification, hydration, and cracking reactions is promoted by addition of a strong acid such as sulphuric acid, phosphoric acid, hydrochloric acid, hydrofluoric acid or para-toluene sulphonic acid. The further addition of water to the reaction can extend the life of the clay catalyst and in some cases its catalytic activity.

13 Claims, No Drawings

METHOD FOR PROMOTING THE ACTIVITY OF CATION-EXCHANGEABLE LAYERED CLAY AND ZEOLITE CATALYSTS IN PROTON-CATALYSED REACTIONS

The present invention relates to a method for promoting the activity of cation-exchangeable layered clay and crystalline aluminosilicate (zeolite) catalysts in esterification, hydration, etherification and cracking reactions.

Crystalline hydrated aluminosilicates, generally referred to as zeolites, are abundant in nature, there being over 34 species of zeolite minerals. Their synthetic preparation by crystallization from aqueous systems containing the necessary chemical components has been investigated since the latter half of the nineteenth century and has led to about 100 types of synthetic zeolite. Zeolites may be represented by the empirical formula:

$$M_{2/n}O.Al_2O_3.xSiO_2.yH_2O$$

in which n is the valence of M which is generally an element of Groups I or II, in particular sodium, potassium, magnesium, calcium, strontium or barium and x is generally equal to or greater than 2. In some synthetic zeolites aluminium cations have been substituted by gallium and silicon atoms by germanium or phosphorus. Zeolites have skeletal structures which are made up of three dimensional networks of $SiO_4$ and $AlO_4$ tetrahedra, corner-linked to each other by shared oxygen atoms. There are no unshared oxygen atoms in the anionic framework so that the ratio of total aluminium and silicon atoms (Al+Si) to oxygen atoms is 1:2 and the negative charges created by the replacement of Si(IV) atoms by Al (III) atoms are neutralised by an electrochemical equivalent of cations (M). The cations (M) in the mineral or originally formed zeolite are exchangeable with other cations. Prior to the mid 1960s it had not been found possible to synthesise zeolites having a silica to alumina molar ratio greater than about 11:1. Thereafter this was achieved by the use of one or more quaternary alkylammonium compounds such as tetramethylammonium, tetraethylammonium, tetrapropylammonium and tetrabutylammonium compounds in the preparation of the zeolite. There resulted a range of crystalline aluminosilicates having a silica to alumina ratio up to 100:1, high stability and extremely high acidity, which latter property renders them particularly useful as catalysts in proton-catalysed reactions such as esterification, hydration, etherification and cracking.

Natural and synthetic clays having a lamellar structure with interlamellar spaces disposed between the lamellar layers are well known. Smectites, such as bentonite, montmorillonites and chlorites are a class of clays possessing such a lamellar structure. Montmorillonite has an idealised stoichiometric composition corresponding to $Na_{0.67}Al_{3.33}Mg_{0.67}(Si_8)O_{20}(OH)_4$. Structurally montmorillonite comprises a central octahedral co-ordination layer containing aluminium and magnesium oxides and hydroxides sandwiched between two tetrahedral co-ordination layers containing silicon oxide. These three layers are tightly bound together and form a single lamellar layer. Normally in nature $Na^+$ or $Ca^{2+}$ ions are present to compensate for the charge imbalance caused by isomorphous substitution of $Mg^{2+}$ or other ions for $Al^{3+}$ in the octahedral layer, and/or $Al^{3+}$ or other ions for $Si^{4+}$ in the tetrahedral layers. The space between the lamellar layers, i.e. the interlamellar space, in the naturally occurring clays is normally occupied by exchangeable $Ca^{2+}$ or $Na^+$ ions. The distance between the interlamellar layers can be increased substantially by absorption of various polar molecules such as water, ethylene glycol, amines, etc., which enter the interlamellar space and in doing so push the layers apart. The interlamellar spaces tend to collapse when the molecules occupying the space are removed by, for example, heating the clays at high temperature.

In the Journal of Catalysts 58, 238–252 (1979) Adams et al. have disclosed that cation exchangeable water-intercalated clays such as water-intercalated montmorillonites in which the exchangeable ions are certain metal cations are catalysts for the conversion of alkenes to the corresponding bis-sec-alkyl ethers. Under the conditions described in this paper the reactants would be present in the liquid phase.

Our European patent publications Nos. 0031252 and 0031687 describe the use of cation-exchangeable layered clays in proton-catalysed reactions e.g. the hydration of olefins to form alcohols, and esterification, either of the type whereby an acid is reacted with an alcohol to form the ester or of the type whereby an olefin is reacted with a carboxylic acid to form the ester.

We have found that the catalytic activity of both cation-exchangeable layered clay and crystalline aluminosilicate catalysts in esterification, hydration, etherification and cracking reactions can be unexpectedly enhanced by the addition of a strong acid. This effect is to be distinguished from the conventional technique for restoring the activity of acid impregnated catalysts whereby further acid is intermittently fed to replace acid leached from the catalyst support during the reaction, such as in the hydration of ethylene over silica supported phosphoric acid.

The present invention therefore provides a method for promoting the activity of a cation-exchangeable layered clay or crystalline aluminosilicate catalyst in esterification, hydration, etherification and cracking reactions which method comprises the addition of a strong acid.

With regard to the catalyst the cation exchangeable layered clay may be selected from those normally classified as smectites or vermiculites. Examples of suitable layered clay minerals include montmorillonites, bentonites, hectorites, beidellites, vermiculites, nontronite and Fullers earths. The cation-exchangeable crystalline aluminosilicate may also be chosen from a wide range of both naturally occurring and synthetic zeolites. Examples of naturally occurring zeolites include offrotite, ferrierite, and mordenite. Typical zeolites and methods for preparing them are described in U.S. Pat. No. 2,882,243 (zeolite A), U.S. Pat. Nos. 2,882,244 (zeolite X), 3,130,007 (zeolite Y), 3,247,195 (zeolite ZK-5), 3,314,752 (zeolite ZK-4), U.K. Pat. No. 1,161,974 (MFI), U.K. Pat. No. 1,334,243 (ZSM-8), U.S. Pat. No. 3,709,979 (MEL), U.K. Pat. No. 1,365,317 (ZSM-12), U.S. Pat. No. 4,016,245 (ZSM-35), European patent publication Nos: 2899 and 2900.

The original nomenclature of some of these synthetic zeolites has been revised, where possible, according to the recommendations of the IUPAC Commission under the chairmanship of Prof R. M. Barrer (Chemical Nomenclature and Formulation of Compositions of synthetic and Natural Zeolites, IUPAC Yellow Booklet, 1978). The aforegoing list is only intended to be representative of the various types of zeolite which may be used in the method of the invention and is not intended to be exhaustive.

As mentioned hereinbefore the clays in their natural state normally contain exchangeable sodium or calcium ions in the interlamellar space and the zeolites contain exchangeable cations (M) which may be either metal or organic cations or mixtures thereof. Such clays and zeolites generally have some catalytic activity but generally it is preferred to exchange some or all of the exchangeable ions with other cations in order to increase their catalytic activity. Ion-exchange is a technique well known in the art. Although any of the variants of that technique may be used for zeolites, in the case of clays it is preferred to use a method which avoids the use of excessively high temperatures which destroy the lamellar structure of the clay, such as may be encountered during calcination for example. Techniques for separating the cation-exchanged clay from the ion exchange media and excess ions are also well known. Any suitable solid/liquid separation procedure followed by repeated resuspension of the solid in distilled water to remove excess cations and reseparation can be used. Decantation or centrifugation are two preferred methods for solid/liquid separation. The nature of the cation which is exchanged on to the clay or zeolite will depend on the type of reaction which the exchanged clay or zeolite is to catalyze. Generally the preferred cation is hydrogen. Other suitable cations include aluminum, cobalt, nickel, iron, copper, vanadium, ammonium, magnesium and calcium ions.

The method of the invention is applicable to the following types of reaction:

(i)
  (a) the formation of esters by the reaction of an alcohol with a carboxylic acid. The conditions under which this reaction is carried out are well known in the art.
  (b) the formation of esters by the reaction of an olefin with a carboxylic acid. With regard to the olefin reactant any olefin may be employed. Suitable olefins include ethylene, propylene, butenes, pentenes and hexenes and diolefins such as butadiene. Mixtures of olefins may also be used if so desired. Both aromatic and aliphatic carboxylic acids may be used. Suitable aliphatic acids include formic, acetic, propionic and butyric acids. Of the aromatic acids benzoic acid and phthalic acids, especially ortho-phthalic acid, may be employed. Preferably the olefin is ethylene, the carboxyic acid is acetic acid and the ester produced is ethyl acetate. The conditions under which the reaction may be carried out are described in our European patent publication Nos. 0031687 and 0031252.

(ii)
  the formation of alcohols by the hydration of olefins. Suitable olefins include ethylene, propylene and butenes. Preferably the olefin is ethylene and the alcohol produced is ethyl alcohol. The conditions under which this reaction may be carried out are well established in the art.

(iii)
  (a) the formation of ethers by the reaction of an alcohol with an olefin. Suitable alcohols include methanol, ethanol, propanols, butanols, pentanols and hexanols, of which linear alcohols are preferred. Diols, polyols and arylalcohols may also be employed. With regard to the olefin any suitable olefin may be employed. Suitable olefins include ethylene, propylene, butenes, pentenes and hexenes, diolefins such as butadiene and cyclic olefins such as cyclohexene. Preferably the olefin is a $C_3$ to $C_6$ linear or branched olefin. Mixtures of olefins such as those commonly encountered in refinery streams may also be used if so desired. Preferably the alcohol is methanol, the olefin is isobutene and the ether produced is methyl tertiary butyl ether. The conditions under which the reaction may be carried out are described in our European patent publication Nos. 0031687 and 0031252.
  (b) the formation of bis-sec-butyl ethers by reaction of a primary or secondary aliphatic alcohol or a polyol. With regard to the primary aliphatic alcohol reactant suitable alcohols include $C_1$ to $C_8$ alkan-1-ols. As regards the secondary aliphatic alcohol, suitable alcohols include straight-chain alcohols, such as $C_3$ to $C_6$ alkan-2-ols, and cyclohexanol. Suitable polyols include alkylene glycols such as ethylene glycol and diethylene glycol. Mixtures of alcohols and/or polyols may also be used if so desired. The reaction may be carried out at a temperature in the range 100° to 300° C., preferably from 150° to 225° C.

(iv)
  the cracking of hydrocarbons. This reaction is so well known that it requires no further elaboration as to suitable feeds and reaction conditions.

In those reactions requiring for their efficient operation the use of temperatures in excess of those at which a clay loses its lamellar structure it is preferred to use a zeolite as the catalyst.

With regard to the strong acid it is believed that the acid must be capable of enhancing the formation of carbonium ions in the catalyst environment. The term "strong acid" within the context of the present specification means an acid having a lower pKa value than acetic acid and which does not combine with the reactants to form a reaction product or products. Suitable strong acids include both mineral acids and organic acids. Examples of suitable strong acids include sulphuric acid, phosphoric acid, hydrochloric acid, hydrofluoric acid and paratoluene sulphonic acid. The strong acid may suitably be added in an amount up to 10% by weight, preferably up to 5% by weight, even more preferably up to 2.0% by weight, based on the total weight of the ractants. Provided that the strong acid is present during the reaction it may be added to the clay or zeolite prior to addition of the reactants or it may be added with the reactants, or both.

A problem sometimes associated with the use of cation-exchangeable layered clays and zeolites in proton-catalyzed reactions when they are carried out continuously is their decline in catalytic activity over relatively short periods. Although the addition of a strong acid can improve the activity of the catalyst, it may only marginally improve the life of the catalyst. We have now unexpectedly found that the addition of water and a strong acid can substantially extend the life of the cation-exchangeable layered clay catalyst and in some cases can also improve its catalytic activity. It is therefore preferred to add water and strong acid when a cation-exchangeable clay is employed as catalyst. Of course, as the man skilled in the art will readily appreciate, in the hydration of olefins, water is one of the reactants and it is therefore difficult to establish the beneficial effect of this feature of the invention in the reaction.

The water may suitably be added in an amount up to 20% by weight, preferably up to 10% by weight, based on the total weight of the reactants.

Although the reactions may be carried out batchwise they are preferably operated in a continuous manner. Furthermore the reactions may be carried out in the liquid phase or in the vapour phase, preferably in the liquid phase.

The invention will now be illustrated by reference to the following Examples and Comparison Tests. In the Examples and Comparison Tests reference will be made to cation-exchanged bentonite and hydrogen ion-exchanged zeolite. These are prepared as follows:

Cation-exchanged bentonite

Sodium bentonite (Wyoming deposit) was immersed in dilute aqueous solutions of (a) sulphuric acid, (b) an aluminium salt, and (c) a copper salt. The clay was washed to remove all extraneous ions and dried at 80° C. to give (a) hydrogen bentonite, (b) aluminum bentonite, and (c) copper bentonite.

Hydrogen ion-exchanged zeolite

Alumina, Laporte Type A, (17 g) was dissolved in a hot solution of sodium hydroxide (26 g) in deionised water (250 ml) and the cooled solution added with stirring to Ludox colloidal stilica (1 kg, 30% silica) and deionised water (750 ml). To this mixture, cooled to 5° C., was added a solution of ethylene oxide (110 g) and "910" ammonia solution (420 ml, 25% ammonia) previously mixed at 5° C.

The resulting mixture was heated at 170° C. for 60 hours in a revolving stainless steel pressure vessel. The resulting solid product was filtered off and washed with deionised water. The filter cake was suspended in a 1 molar aqueous solution of ammonium chloride (1.51) and heated with stirring for one hour. This operation was carried out three times. The solid aluminosilicate so prepared was filtered off, washed with water, dried at 120° C. for 16 hours, and calcined in air at 500° C. (4–16 hours) to give the hydrogen ion-exchanged zeolite.

Comparison Test 1

Acetic acid (80 g) and hydrogen bentonite (10 g) in the form of a fine powder were added to a 100 ml stirred stainless steel autoclave which was then sealed. The autoclave was pressurized with ethylene to the extent that a pressure of 55 bar would be obtained at 200° C. The autoclave was then heated to a temperature of 200° C. and maintained at this temperature for 2.5 hours. At the end of this period the autoclave was allowed to cool and the gases vented off. The liquid products were examined and found to contain 35.0% wt. ethyl acetate produced from acetic acid with a selectivity of >99%.

This is not an example according to the invention because no strong acid was added to the reactants. It is included only for the purpose of comparison.

EXAMPLE 1

Comparison Test 1 was repeated except that 0.1 g concentrated sulphuric acid was added to the acetic acid reactant. The results are shown in Table 1.

EXAMPLE 2

Comparison Test 1 was repeated except that 0.2 g concentrated sulphuric acid was added to the acetic acid reactant. The results are shown in Table 1.

EXAMPLE 3

Comparison Test 1 was repeated except that 0.5 g concentrated sulphuric acid was added to the acetic acid reactant. The results are shown in Table 1.

TABLE 1

| Example No. | Weight of concentrated sulphuric acid added to acetic acid reactant (g) | Weight ethyl acetate in liquid products (%) | Selectivity of conversion of acetic acid to ethyl acetate (%) |
|---|---|---|---|
| Comp. Test 1 | 0 | 35.0 | >99 |
| Example 1 | 0.1 | 41.3 | " |
| Example 2 | 0.2 | 43.7 | " |
| Example 3 | 0.5 | 53.2 | " |
| Example 4 | 1.0 | 46.5 | " |
| Comp. Test 2 | 0.5 | trace | — |

EXAMPLE 4

Comparison Test 1 was repeated except that 1.0 g concentrated sulphuric acid was added to the acetic acid reactant. The results are shown in Table 1.

Comparison Test 2

Example 3 was repeated except that the addition of hydrogen bentonite was omitted. The results are shown in Table 1.

This is not an example according to the present invention because neither a layered clay nor a crystalline aluminosilicate was employed. It is included only for the purpose of comparison.

The results reported in Table 1 demonstrate that hydrogen bentonite is an active catalyst for the reaction of ethlene and acetic acid to form ethyl acetate in the absence of added strong acid. Concentrated sulphuric acid alone is not an active catalyst for the reaction. However the results of Examples 1 to 4 demonstrate that the addition of concentrated sulphuric acid to the acetic acid reactant increases the amount of ethyl acetate in the liquid products i.e. it promotes catalytic activity.

Comparison Test 3

Comparison Test 1 was repeated except that the hydrogen bentonite was replaced by aluminum bentonite. The results are shown in Table 2.

EXAMPLE 5

Comparison Test 3 was repeated except that 0.5 g concentrated sulphuric acid was added to the acetic acid reactant. The results are shown in Table 2.

Comparison Test 4

Comparison Test 1 was repeated except that copper bentonite was used in place of hydrogen bentonite. The results are given in Table 2.

EXAMPLE 6

Comparison Test 4 was repeated except that 0.5 g concentrated sulphuric acid was added with the acetic acid reactant. The results are shown in Table 2.

Comparison Test 5

Comparison Test 1 was repeated except that hydrogen bentonite was replaced by sodium bontonite. The results are given in Table 2.

TABLE 2

| Example No. | Catalyst Cation | Weight of concentrated sulphuric acid added to acetic acid reactant. (g) | Weight ethyl acetate in liquid products (%) | Selectivity of acetic acid conversion to ethyl acetate (%) |
|---|---|---|---|---|
| Comp. Test 1 | Hydrogen | 0 | 35.0 | >99 |
| Example 3 | " | 0.5 | 53.2 | " |
| Comp. Test 3 | Aluminium | 0 | 16.0 | " |
| Example 5 | " | 0.5 | 47.4 | " |
| Comp. Test 4 | Copper | 0 | 10.1 | " |
| Example 6 | " | 0.5 | 36.5 | " |
| Comp. Test 5 | Sodium | 0 | 0.7 | " |
| Example 7 | " | 0.5 | 6.7 | " |
| Example 8 | " | 1.0 | 35.1 | " |

EXAMPLE 7

Comparison Test 5 was repeated except that 0.5 g concentrated sulphuric acid was added to the acetic acid reactant. The results are given in Table 2.

EXAMPLE 8

Comparison Test 5 was repeated except that 1.0 g concentrated sulphuric acid was added to the acetic acid reactant. The results are given in Table 2.

The results presented in Table 2 demonstrate that aluminum bentonite, copper bentonite and sodium bentonite catalyse the reaction of ethylene with acetic acid to form ethyl acetate, though their activity is very much inferior to that of hydrogen bentonite. The addition of concentrated sulphuric acid promotes the activity of aluminum bentonite, copper bentonite and sodium bentonite to better or comparable levels than are observed for the unpromoted hydrogen bentonite.

Comparison Test 6

Comparison Test 1 was repeated except that hydrogen bentonite was replaced by a hydrogen ion-exchanged zeolite prepared as hereinbefore described. The results are given in Table 3.

EXAMPLE 9

Comparison Test 6 was repeated except that 0.5 g concentrated sulphuric acid was added to the acetic acid reactant. The results are given in Table 3.

The results presented in Table 3 demonstrate that hydrogen ion-exchanged zeolite is an active catalyst for the reaction of ethylene with acetic acid to form ethyl acetate. The addition of concentrated sulphuric acid considerably enhances the activity of the catalyst.

Comparison Test 7

A reactor was charged with 20 ml of hydrogen bentonite prepared in the manner hereinbefore described in the form of 200-280 mm mesh particle size and mixed with 20 ml inert ⅛ inch cylinder packing to facilitate a better liquid flow path through the catalyst bed. Glacial acetic acid was pumped through the catalyst bed at a rate of 40 ml/hour, providing a LHSV of 2 (calculated on active catalyst). The reactor was maintained at 40-50 bar ethylene pressure with a constant flow of ethylene over the catalyst.

TABLE 3

| Example No. | Weight of concentrated sulphuric acid added to acetic acid reactant (g) | Weight ethyl acetate in liquid products (%) | Selectivity of conversion of acetic acid to ethyl acetate (%) |
|---|---|---|---|
| Comp. Test 6 | 0 | 15 | >99 |
| Example 9 | 0.5 | 41.4 | 98 |

A particular start-up sequence was used so as not to deactivate the catalyst prior to reaction. Acetic acid was fed into the reactor to saturate the catalyst bed at a temperature of ca. 100°-120° C. after which ethylene was allowed into the reactor and the system allowed to reach working pressure. The temperature was then raised to a working value of 200° C. which was reached within 2 hours of start-up.

The initial activity of this catalyst under the reaction conditions was 30% conversion of the acetic acid to ethyl acetate. The conversion gradually declined and the catalyst half-life was judged to be about 18 hours.

EXAMPLE 10

Comparison Test 7 was repeated except that 2.5% water and 2.5% concentrated sulphuric acid, both percentages being by weight, were added to the acetic acid feedstock.

The initial activity of 22-23% conversion of acetic acid to ethyl acetate increased so that at the termination of the reaction after some 75 hours on stream the activity had increased to the extent that a 37% yield of ethyl acetate was obtained.

The results of Comparison Tests 7 and Example 10 demonstrate that the decline in activity of the clay catalyst can be substantially retarded by the addition of both strong acid and water.

We claim:

1. A method for promoting the activity of a cation-exchangeable layered clay or a zeolite catalyst in an esterification reaction which comprises carrying out such as reaction in the presence of said catalyst and in the presence of a strong acid.

2. A method for promoting the activity of a cation-exchangeable layered clay or a zeolite catalyst in an esterification reacton which comprises reacting an olefin with a carboxylic acid in the presence of said catalyst and a strong acid.

3. A method according to claim 2 wherein the carboxylic acid is acetic and the ester produced is ethyl acetate.

4. A method according to claim 1, 2 or 3 wherein the clay or zeolite is exchanged with one or more of chromium, cobalt, nickel, iron, copper, vanadium, ammonium, magnesium and calcium ions.

5. A method according to claim 1, 2 or 3 wherein the clay or zeolite is exchanged with hydrogen ions.

6. A method according to claim 1 wherein the reaction is the formation of esters by the reaction of an alcohol with a carboxylic acid.

7. A method according to claim 1, 2 or 3 wherein the strong acid is either sulphuric acid, phosphoric acid, hydrochloric acid, hydrofluoric acid or para-toluene solphonic acid.

8. A method according to claim 1, 2 or 3 wherein the strong acid is added in an amount up to 10% by weight, based on the total weight of the reactants.

9. A method according to claim 8 wherein the strong acid is added in an amount up to 2.0% by weight.

10. A method according to claim 1, 2 or 3 wherein water is also added.

11. A method according to claim 10 wherein the water is added in an amount up to 20% by weight, based on the total weight of reactants.

12. A method according to claim 11 wherein water is added in an amount up to 10% by weight.

13. A method according to claim 1, 2 or 3 wherein said acid is added to a reactant.

* * * * *

UNITED STATES PATENT AND TRADEMARK OFFICE
CERTIFICATE OF CORRECTION

PATENT NO.  : 4,440,958
DATED       : April 3, 1984
INVENTOR(S) : REGINALD GREGORY et al It is certified that error appears in the above-identified patent and that said Letters Patent is hereby corrected as shown below:

Col. 3, line 29, After "aluminum" word --chromium-- has been omitted.

Col. 3, line 49, "carboxyic" should read --carboxylic--

Col. 4, line 12, "bis-sec-butyl" should read --bis-sec-alkyl--

Col. 4, line 47, "ractants" should read --reactants--

Col. 5, line 38, "stilica" should read --silica--

Col. 6, line 46, "ethlene" should read --ethylene--

Col. 7, line 9, "bontonite" should read --bentonite--

Col. 9, line 12, Claim 3, After "acetic" word --acid-- has been omitted.

Col. 9, line 2, Claim 1, "as" should read --a--

Col. 10, line 7, Claim 7, "solphonic" should read --sulphonic--

Signed and Sealed this

Second Day of April 1985

[SEAL]

Attest:

DONALD J. QUIGG

Attesting Officer      Acting Commissioner of Patents and Trademarks